United States Patent

Imran et al.

[11] Patent Number: 5,542,434
[45] Date of Patent: Aug. 6, 1996

[54] GUIDE WIRE WITH DEFLECTABLE TIP AND METHOD

[75] Inventors: Mir A. Imran, Palo Alto; Deepak R. Gandhi, San Jose; Henry Bourang, Turlock; Dignah B. Quiachon, Palo Alto; Andrew Y. Chow, Sunnyvale, all of Calif.

[73] Assignee: Intelliwire Inc., Sunnyvale, Calif.

[21] Appl. No.: 331,216

[22] Filed: Oct. 28, 1994

[51] Int. Cl.⁶ .................................................. A61B 5/00
[52] U.S. Cl. ............................................ 128/772; 604/281
[58] Field of Search ............................... 128/657, 658, 128/772; 604/280–282

[56] References Cited

U.S. PATENT DOCUMENTS

| | | | |
|---|---|---|---|
| 5,052,404 | 10/1991 | Hodgson | 128/772 |
| 5,055,101 | 10/1991 | McCoy | 128/772 |
| 5,349,964 | 9/1994 | Imran et al. | 128/772 |
| 5,415,633 | 5/1995 | Lazarus et al. | 128/772 |
| 5,433,200 | 7/1995 | Fleishhacker | 128/772 |

*Primary Examiner*—Max Hindenburg
*Attorney, Agent, or Firm*—Flehr, Hohbach, Test, Albritton & Herbert

[57] ABSTRACT

Guide wire for use in a medical procedure and for use with the power supply comprising a flexible elongate tubular member having proximal and distal extremities and having a bore extending from the proximal extremity to the distal extremity. A core wire extends through the bore of the flexible elongate tubular member. A coil assembly is mounted on the distal extremity of the flexible elongate member and has a distal extremity. A rounded tip is formed on the distal extremity. An actuator member has at least a portion thereof disposed in the coil assembly and has proximal and distal extremities. The proximal extremity of the actuator member is secured to the distal extremity of the flexible elongate tubular member. The distal extremity of the actuator member is secured to the rounded tip. The actuator member has a portion thereof formed of a shape memory material and incorporating a shape member therein. A heater is disposed in the vicinity of said portion of the actuator member for heating said portion to cause it to assume the predetermined shape memory. Electrical conductors are connected to the heater and extending to the proximal extremity of the flexible elongate tubular member and are adapted to be connected to the power supply to supply energy to the heater.

20 Claims, 4 Drawing Sheets

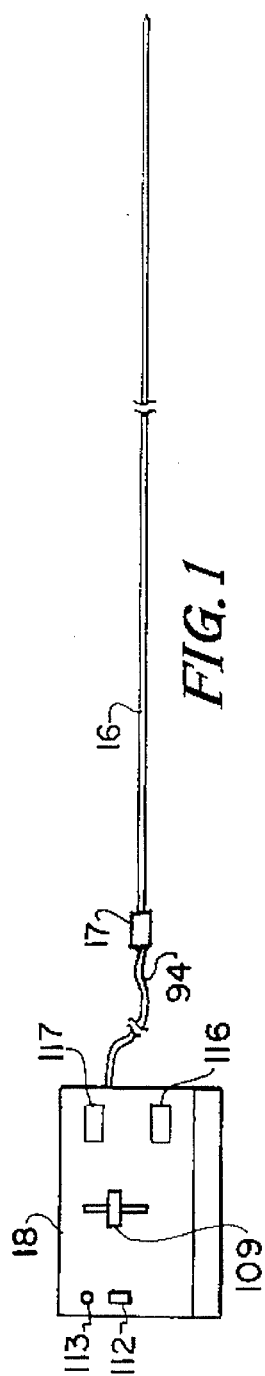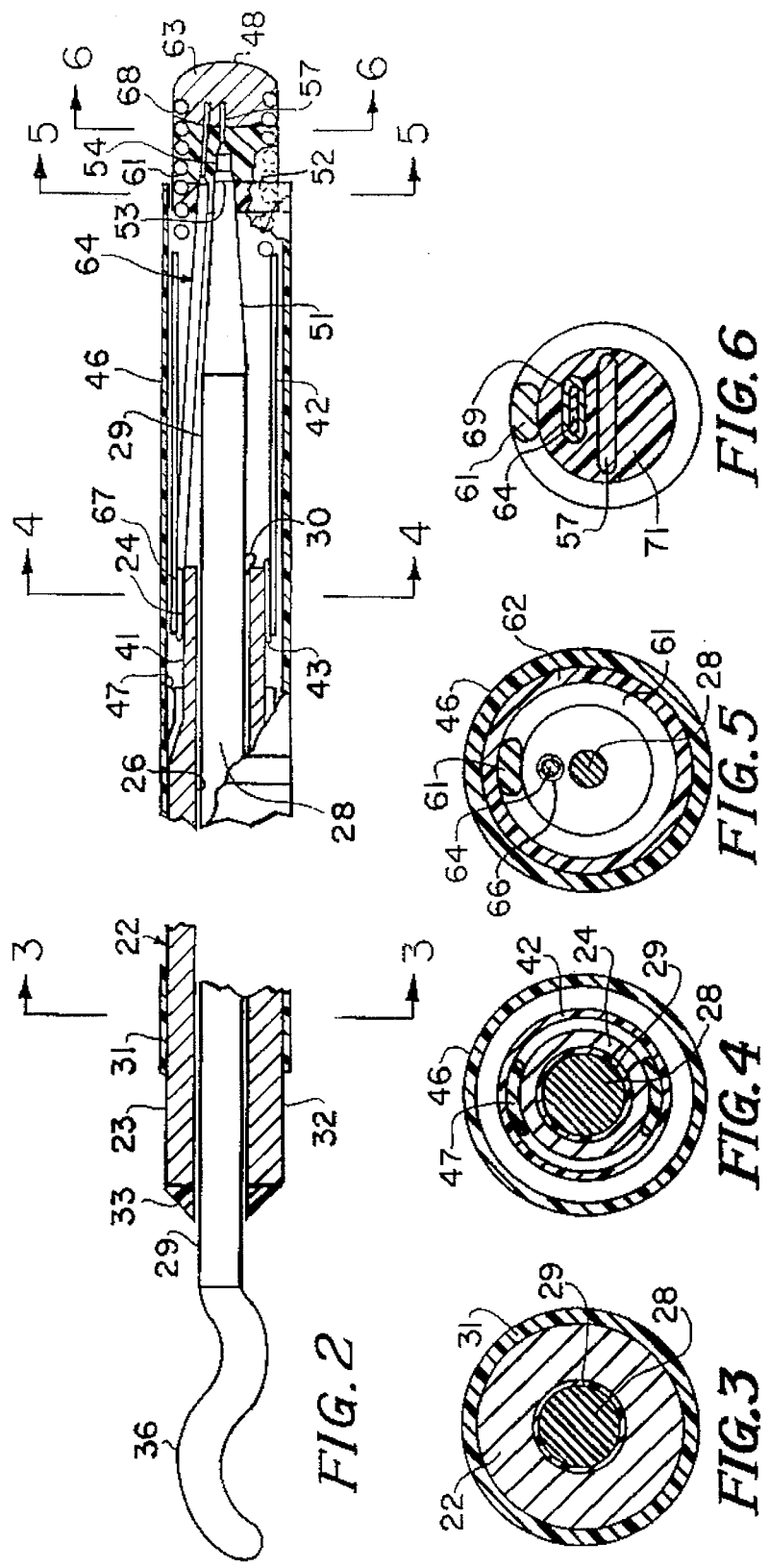

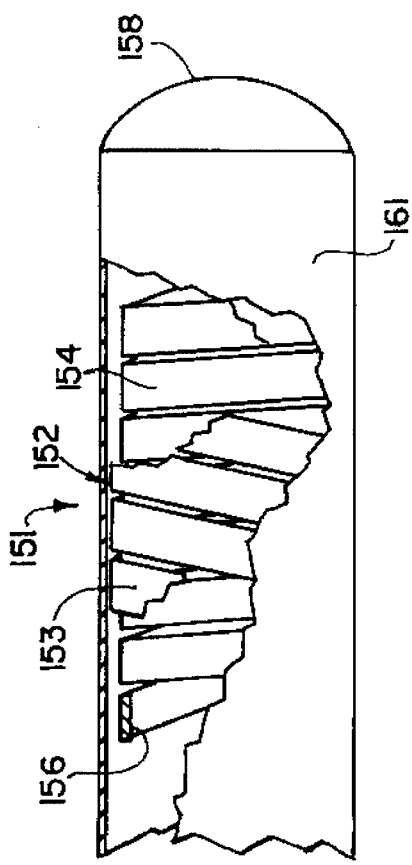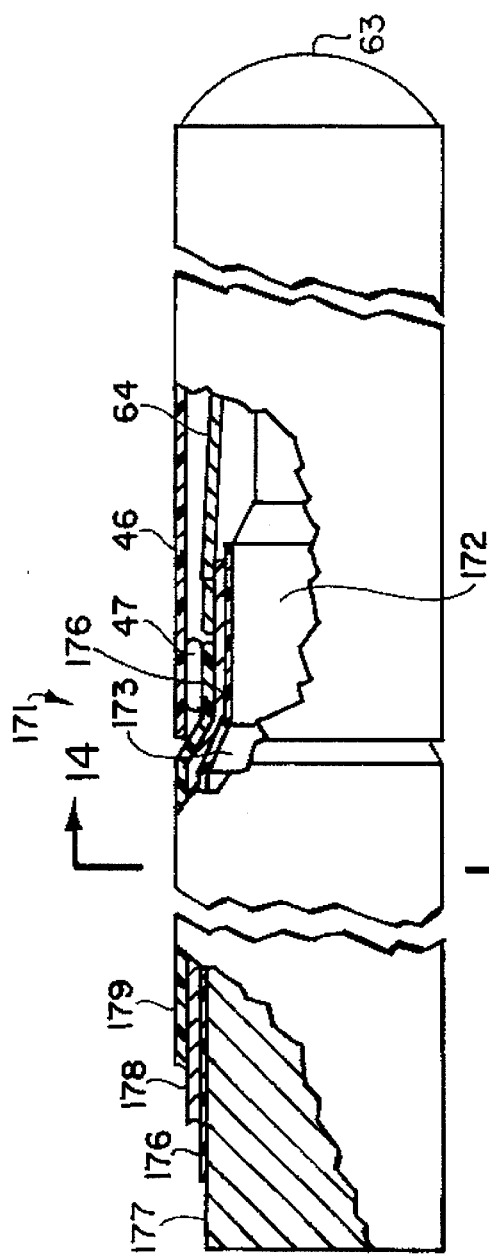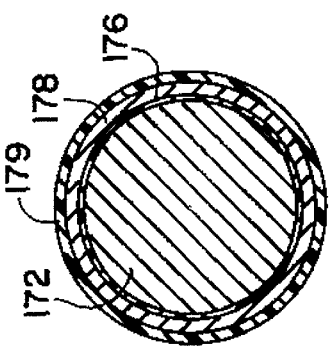

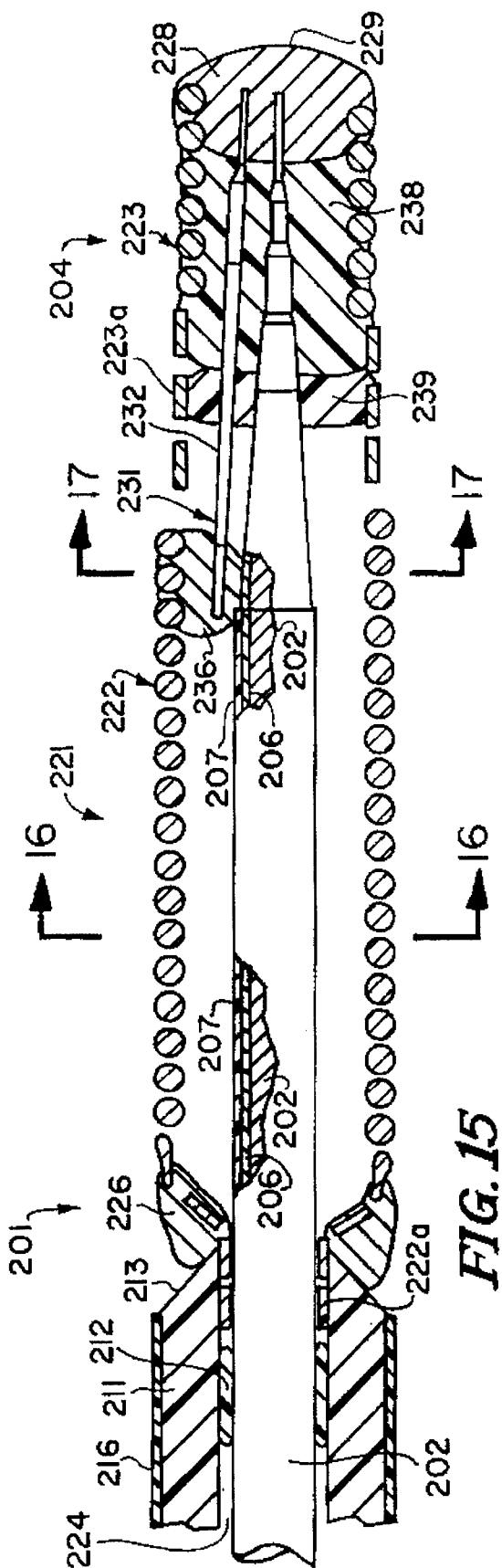
FIG.15
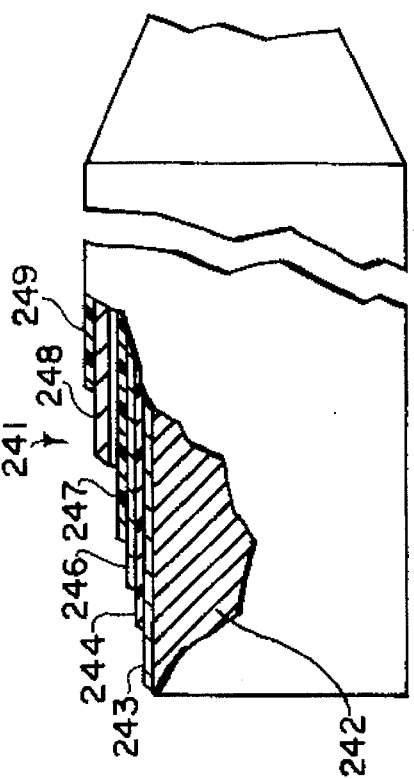
FIG.18
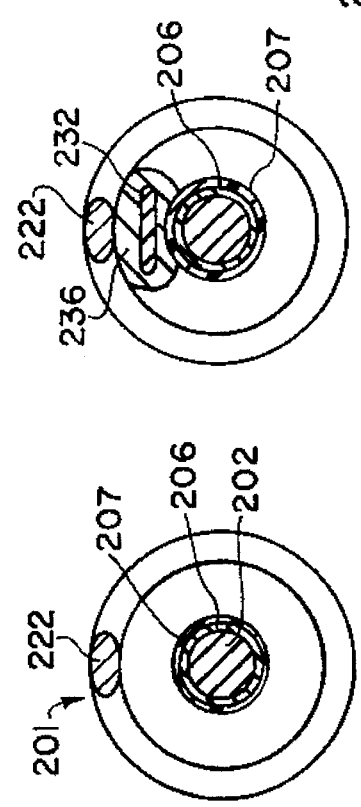
FIG.17
FIG.16

GUIDE WIRE WITH DEFLECTABLE TIP AND METHOD

This invention relates to guide wires with deflectable tips and a method.

Guide wires have been available in the past for many different applications including medical applications such as coronary angioplasty. In guide wires heretofore provided for angioplasty applications, such guide wires have been provided with flexible tips which typically can be shaped outside the body and then introduced into the body. With such a procedure it is often necessary to remove the guide wire from the body and reshape the distal extremity and reinsert the guide wire into the body to negotiate a tortuous vessel. Therefore there is a need for a guide wire that does not have such limitations.

In general, it is the object of the present invention to provide a guide wire with a deflectable tip which can be deflected in vivo.

Another object of the invention is to provide a guide wire of the above character which can have diameters ranging from 0.010 inches to 0.038 inches and larger.

Another object of the invention is to provide a guide wire of the above character that can be relatively long in length.

Another object of the invention is to provide a guide wire and method of the above character in which different shapes can be provided in the distal extremity.

Another object of the invention is to include a guide wire and method of the above character in which the different predetermined shapes can be incorporated into the tip.

Another object of the invention is to provide a guide wire and method of the above character in which additional stiffness can be imparted to the distal extremity to facilitate penetration of a stenosis in a vessel.

Another object of the invention is to provide a guide wire and method of the above character in which the distal extremity can be provided with a pre-bend before insertion into the vessel.

Another object of the invention is to provide a guide wire and method of the above character in which localized heating is utilized to minimize the introduction of heat into the bloodstream in the vessel.

Another object of the invention is to provide a guide wire and method of the above character in which various degrees of floppiness can be achieved in the distal extremity.

Another object of the invention is to provide a guide wire and method of the above character in which the tip can be deflected in substantially real time.

Another object of the invention is to provide a guide wire and method of the above character in which coaxial conductors are utilized to maximize the size of the coil wire, to reduce any tendency to whip and to facilitate manufacture.

Additional objects and features of the invention will appear from the following description in which the preferred embodiments are set forth in detail in conjunction with the accompanying drawings.

FIG. 1 is a side elevational view of guide wire having a deflectable tip with a control console incorporating the present invention.

FIG. 2 is an enlarged view of partially in section of the guide wire, shown in FIG. 1.

FIG. 3 is a cross sectioned view taken along the line 3—3 of FIG. 2.

FIG. 4 is a cross-sectional view taken along the line 4—4 of FIG. 2.

FIG. 5 is a cross-sectional view taken along the line 5—5 of FIG. 2.

FIG. 6 is a cross-sectional view taken along the line 6—6 of FIG. 2.

FIG. 12 is an isometric side elevational view partially in section of another embodiment of a guide wire incorporating the present invention.

FIG. 13 is a partial side elevational view showing the distal extremity of another embodiment of a guide wire incorporating the present invention.

FIG. 14 is a cross-sectional view taken along the line 14—14 of FIG. 13.

FIG. 15 is a side elevational view partially in section of the distal extremity of another embodiment of a guide wire incorporating the present invention.

FIG. 16 is a cross-sectional view taken along the line 16—16 of FIG. 15.

FIG. 17 is a cross-sectional view taken along the line 17—17 of FIG. 15.

FIG. 18 is a partial side elevational view partially in section of another embodiment of the guide wire incorporating the present invention.

Figure 7:
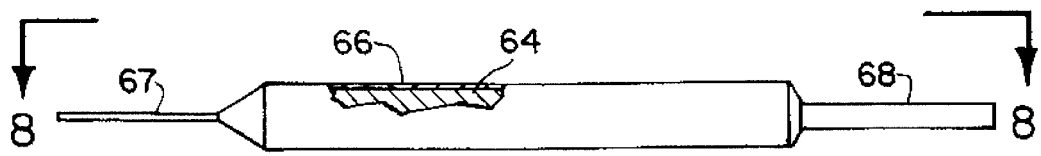
FIG. 7 is a side elevational view of the actuator wire utilized in the guide wire shown in FIG. 1.
Figure 8:
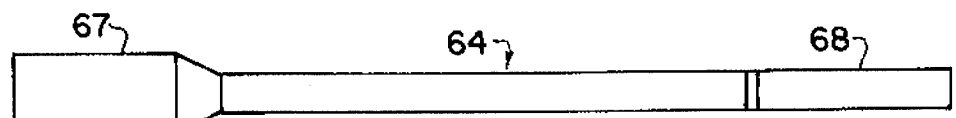
FIG. 8 is a plan view of the actuator wire shown in FIG. 7 looking along the line 8—8 of FIG. 7.

In general, the guide wire of the present invention is for use in a medical procedure and for use with a power supply. The guide wire is comprised of a core wire having proximal and distal extremities. A coil assembly is mounted on the distal extremity of the core wire and has a distal extremity. A rounded tip is carried by the distal extremity of the coil assembly. An actuator member as provided having at least a portion thereof disposed in the coil assembly and having proximal and distal extremities. Means is provided for securing the distal extremity of the actuator member to the rounded tip. The actuator member has a portion thereof formed of a shape memory material and incorporating a shape memory therein. Heating means is disposed in the vicinity of said portion of the actuator member for heating said portion to cause it to assume the predetermined shape memory. Electrical conductive means is connected to the heating means and extends to the proximal extremity of flexible elongate tubular member and is adapted to be connected to the power supply to supply energy to the heating means.

More particularly as shown in FIGS. 1–10, the guide wire 16 shown therein is of the type which is particularly adapted for coronary and cardiology applications. It is connected to a connector assembly 17 connected to a control console 18. The guide wire 16 consists of a flexible elongate tubular member 22 having proximal and distal extremities 23 and 24. The flexible elongate tubular member 22 can be formed of a suitable material such as stainless steel, having a suitable outside diameter, as for example 0.013 inches and a wall thickness ranging from 0.0015 to 0.0035". The guide wire 16 can have a suitable length as for example 175 to 180 cms with the flexible elongate tubular member 22 in such an embodiment having a suitable length as for example 150 cms. The flexible elongate tubular member 22 is provided with a bore 26 of a suitable diameter as for example 0.009 to 0.010" extending from the proximal extremity 23 to the distal extremity 24. The inside diameter of the flexible elongate tubular member 22 which often is called a hypo tube in the present embodiment has an inside diameter of approximately 0.006" to 0.018" and preferably 0.010" which would mean that the 0.0014" outside diameter hypo tube would have a nominal wall thickness of 0.002".

An inner mandrel or core wire 28 also formed of a suitable material such as stainless steel and having suitable diameter as for example 0.006" is disposed in the bore 26 and extends the length thereof. Generally it is desirable that the inner mandrel or core wire 28 have as large a diameter as possible. Thus with a 0.013" flexible elongate tubular member 22, a core wire can have an outside diameter ranging up to 0.0075 to 0.008" to provide improved torque characteristics. It should be appreciated that the inner mandrel or core wire 28 can be formed of other hybrid materials such as Nitinol and other alloys. The mandrel or core wire 28 tip is heat treated and annealed to prevent whipping of the guide wire 16 as the guide wire 16 is rotated. The outside surface of the core wire 28 is coated with a suitable insulating material as for example a thin wall polyimide coating 29 having a thickness ranging from 0.00025 to 0.0005". This polyimide coating 29 extends the length of the core wire 28 and serves to insulate the core wire 28 from the flexible elongate tubular member 22. The distal extremity 24 of the flexible elongate tubular member 22 is bonded to the core wire 28 by an adhesive 30.

An insulation layer 31 is also provided on the outside surface of the flexible elongate tubular member 22 which can be formed of a suitable material such as polyethylene, polyimide or PET and having a thickness range from 0.0002 to 0.0008". The proximal extremity of the flexible elongate tubular member 22 is not covered by the insulating layer 31 and serves as a sleeve 32 for making electrical contact to the sleeve as hereinafter described. A fillet 33 formed of a suitable adhesive such as a polyurethane provides a transition between the flexible elongate tubular member 22, or in other words a stainless steel hypo tube 22 to the polyimide coating or insulation 29 provided on the core wire 28. It should be appreciated that in place of the adhesive fillet 33, a piece of plastic shrink tubing could be used to make the transition from the stainless steel hypo tube or flexible elongate member 22 to the core wire 28 to provide the desired graduated transition between the same. The proximal extremity of the inner mandrel core wire 28 is not covered with the insulating coating or layer 29 and is crimped or coined to provide an end 36 which can serve as an exchange wire as hereinafter described.

The construction of the guide wire 16 from the cross sections shown in FIG. 3 and FIG. 4 show that the construction is substantially identical from the proximal extremity of the guide wire shown in FIG. 3 to the distal extremity of the flexible elongate tubular member 22 near to the cross section of FIG. 4. As shown in FIG. 2, the distal extremity of the flexible elongate tubular member 22 is tapered to provide a conical portion 41 to reduce outside diameter of the flexible elongate tubular member from about 0.014" to about 0.007". An inner insulating sleeve 42 of a suitable insulating material such as a polyimide has a proximal extremity secured to the distal extremity of the flexible elongate tubular member 22 distal of the taper 41 by suitable means such as an adhesive 43. An outer sleeve 46 of the same or similar insulating material has its proximal extremity secured to the taper 41 of the flexible elongate tubular member 22 with the insulating layer 31 thereon by a suitable means such as an adhesive 47. The insulating layer sleeve 31 extends from the proximal extremity of the flexible elongate tubular member 22 and then extends over the inwardly extending taper 41 and underlies the proximal extremity of the outer insulating sleeve 46 formed of a suitable material such as a polyimide. The inner and outer sleeves 42 and 46 can have suitable outside diameters for example the inner sleeve can have an outside diameter ranging from 0.008" to 0.014" whereas the sleeve 46 can have an outside range from 0.010" to 0.018".

It should be appreciated that the outer insulating sleeve 31 can possibly be eliminated in certain applications. Although in the present construction it does serve to provide some additional insulation and it also serves to protect the flexible elongate tubular member 22 from the blood or other fluid into which the guide wire is inserted. It also should be appreciated that if desired a single shrink tube of insulating material could be substituted for the outer sleeve 46 and the inner sleeve 31 in certain applications.

The flexible elongate tubular member 22 terminates at a distance of approximately 15 to 30 cms from a tip 48 of the guide wire. The core wire 28 extends out of the distal extremity 24 of the flexible elongate tubular member 22 and is of a uniform diameter of approximately 0.008" until approximately 8–12 cms from the tip 48 where it is provided with a centerless ground taper 51 for a distance of 3–5 cm. This is followed by another taper 53 reducing the diameter from 0.0024" to a flat 54 having a thickness of 0.002" and a width of 0.004" and having a length of approximately 1 cm. This is followed by another taper 56 to another flat 57 having a length of approximately 1 cm and having a thickness of 0.001" and a width of 0.006". The flats 54 and 57 provide preferential bending in one direction as hereinafter described.

A coil spring 61 formed of a suitable radiopaque material such as a platinum-tungsten alloy is secured within the distal extremity of the polyimide outer sleeve 46 by suitable means such as an adhesive 62. The coil spring 61 is secured in such a manner so that its proximal extremity abuts the distal extremity of the inner insulating sleeve 42. By way of example the coil spring 61 can be formed of a wire material having a diameter of 0.025" which is wound into a coil having a diameter of 0.0125" and a suitable length as for example 3.5 cms. A weld 63 formed as a round globule can be in the form of a radiopaque solder that adheres to the distal extremity of the coil spring 61 and has embedded therein the distal extremities of the flat 57 of the core wire 28.

Means is provided for causing bending of the distal extremity of the guide wire 16 and consists of an actuator wire 64 formed of a suitable shape memory material such as Nitinol. It is desirable that this shape memory material make a transformation from martensite to austenite between 45° and 60° C. It is desirable that it be a temperature which is above the body temperature of 37° C. but be at a temperature below 70° C. so as to reduce the amount of current required to cause transformation from the martensitic to austenitic phase. The actuator wire 64 should be formed of a nickel titanium alloy which has a narrow hysterises loop. This is desirable because when the wire returns to its martensitic state the guide wire should reach this condition at a temperature above body temperature. In connection with the present invention, it is desirable that the hysterises loop be between 10° and 20°. The overall length of the pull or actuator wire 64 can range from 1 cm to 40 cms in the present embodiment with a preferable length of 17 cms.

The actuator wire 64 is provided with the conductive plating or coating 66 (see FIGS. 5 and 7) formed of a suitable material such as silver having a suitable thickness as for example 0.0002" extending the entire length thereof up to the flattened proximal and distal extremities 67 and 68 as shown in FIG. 7. The proximal extremity 67 is bonded to the distal extremity or taper 41 of the hypotube 22 by suitable means such as a silver epoxy (not shown). The conductive coating 66 is covered with a coating 69 of a suitable insulating material such as the polyimide having a suitable thickness as for example 0.0002 inches. The polyimide coating 69 does not extend over the proximal portion 67 of the actuator wire 64 but does extend over the distal extremity 68 (see FIG. 6).

The silver coating 66 is provided to reduce the resistance of the actuator wire 64 to thereby reduce the power that is necessary to cause deflection of the actuator wire. When the current reaches the unplated distal extremity 68 of the actuator wire 64 the unplated or recoated distal extremity has a higher resistance because of the absence of the plating which causes bending of the distal extremity of the actuator wire 64. Thus with such a construction it is seen that only a minimum amount of heating is imparted to the distal extremity of the guide wire and that this heating is only that required for causing bending of the distal most extremity 68 in accordance with the shape memory which has been placed therein. The shape memory incorporated into the distal extremity 68 can be one which when the distal extremity is heated it will become curved as for example to form a 90° bend or greater or alternatively when heated will assume a straight shape. If the actuator wire 64 is to form a bend standing through more than 90° as for example up to 180° the distal extremity of the guide wire 16 will have a hook-like appearance which typically should not have a diameter which exceeds 2 centimeters. With such a shape memory actuator wire 64, the distal extremity of the guide wire 16 will be normally straight and will only become shaped or take a radius of curvature when the actuator wire 16 is heated to activate the memory which has been placed in the actuator wire 64.

In order to further inhibit the transfer of energy into the blood in which the tip 48 of the guide wire may be immersed, a polyimide 71 such as silicon fills the space in the coil 61 between the weld 63 and the adhesive 62.

In the embodiment of the actuator wire 64 hereinbefore described and shown in FIGS. 2–8, the actuator wire has a diameter of 0.0025". This diameter however can range from 0.001" to 0.005". The proximal end 67 shown in FIGS. 7 and 8 can be flattened so it has a thickness of approximately 0.001" and having the width of approximately 0.005" and having a length ranging from 1 to 2 cms. The distal extremity 68 also has been flattened to a thickness of approximately 0.0015" and can have the same width ranging from 0.002 to 0.004". It can have a length ranging from 1½ to 3 cms. It should be appreciated that the actuator wire 64 can have a rectangular cross section along its entire length to form a ribbon as for example a width of 0.004" to 0.006" and a thickness of 0.0015" to 0.002".

Figure 9:
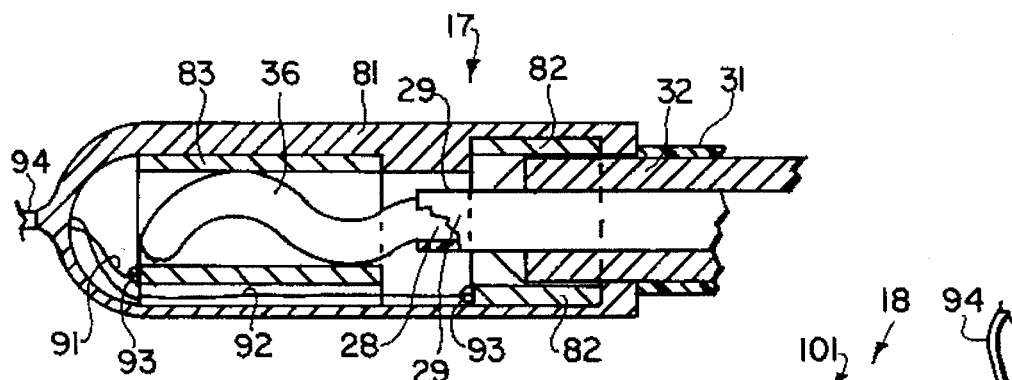
FIG. 9 is a side elevational view partially in section of the connector used with the guide wire shown in FIGS. 1 through 6.

The connector 17 as shown particularly in FIG. 9 consists of a housing 81 formed of a suitable material such as plastic which carries first and second spaced apart conductive sleeves or rings 82 and 83 formed of a suitable material such as beryllium copper. Ring 82 engages and forms a part of the sleeve 32 carried by the flexible elongate tubular member 22. Sleeve 83 is adapted to engage the coined end 36 of the core wire 29. Insulated conductors 91 and 92 formed of a suitable conductive material such as copper are connected by a suitable means such as solder 93 to the rings 82 and 83 and are connected into a cable 94 which is connected to the control console 18. The connector 17 is sized to make a friction fit with the coined end 36 on the proximal extremity 23 of the guide wire 16 so that it can be installed and removed with a small amount of force as for example, 50 to 70 grams. The frictional retaining force should be sufficient to retain the connector 17 connected to the guide wire 16 and not accidentally fall off.

Figure 10:
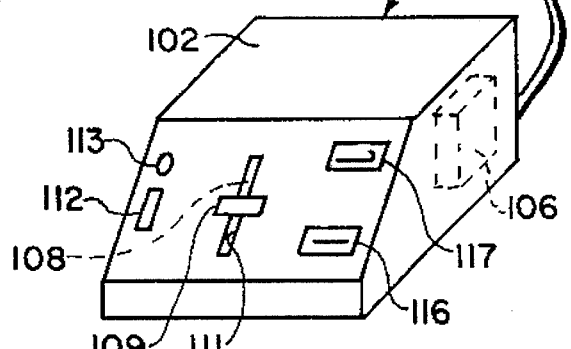
FIG. 10 is an enlarged isometric view of the control console shown in FIGS. 1 through 9.

The control console 18 as shown more specifically in FIG. 10 consists of a housing 101 which is provided with an inclined front panel 102 (see FIG. 10). The housing 101 is provided with an output connector (not shown) which is adapted to receive the cable 94. The housing 101 houses a suitable power supply as for example a battery pack 106. The battery pack 106 is connected to circuitry (not shown) which can be of a conventional type for supplying the power from the battery to a linear potentiometer 108 which has a slider (not shown) connected to a handle 109 that extends through a slot 111 extending upwardly and downwardly of the front panel 102 to control the amount of power supplied to the actuator wire 64. An on/off switch 112 is also mounted on the front panel 102 and a light 113 is mounted on the front panel 102 in the vicinity thereof to indicate when power is on or off. Graphic displays 116 and 117 are provided on the front panel for representing tip deflection with display 117 showing a 90° deflection and display 116 showing a 0° deflection.

Operation and use of such guide wire may now be briefly described as follows. Let it be assumed that it is desired to utilize the guide wire 16 in a conventional angioplasty procedure. The physician removes the guide wire 16 from the package in which it was shipped and let it be assumed that the guide wire 16 has been provided with a shape memory which assumes a bend upon being heated but otherwise will be straight. However, the distal extremity of the guide wire 16 will be very soft to provide an atraumatic floppy tip which is nearly equivalent to the stiffness i.e., or floppiness of a conventional ACS High Torque™ floppy guide wire. The guide wire 16 can be advanced into a guiding catheter which has also already been placed in a vessel of the patient and then advanced into the coronary vessel in which it is desired to obtain access to a stenosis in a coronary vessel.

It should be appreciated that the guide wire 16 can be provided with a torquer of a conventional type to aid in torquing the guide wire 16 during the time it is being advanced into the vessel of the patient. In connection with the present procedure, the guide wire can first be advanced to the desired location and then the angioplasty or balloon catheter advanced over the guide wire to the desired position in the stenosis or alternatively, if desired, a balloon catheter can be preloaded onto the guide wire 16 with the distal extremity of the guide wire 16 extending beyond the catheter. With the entire procedure being viewed fluoroscopically, let it be assumed that the physician reaches a bifurcation in a coronary vessel and that it is desired to advance into a particular branch to reach a stenosis that can only be accomplished by forming curve in the distal extremity of the guide wire 16.

As soon as the physician ascertains that this is necessary, the physician may merely need grasp the handle 109 of the linear potentiometer 108 to supply power to the actuator wire 64. As pointed out previously, the current will flow through the low resistance silver coating 66 into the high resistance distal extremity 68 of the actuator wire 64 to cause heating of the distal extremity 68 to cause it to reach a temperature to cause the material to transfer from an austenitic state to a martensitic state and to thereby cause the tip of the guide wire 16 to begin to bend. As soon as the deflection or bending of the amount desired has occurred by observing the distal extremity fluoroscopically and also viewing the display 117, the physician can advance the guide wire 16 into the desired branch vessel. Because of the low mass of the material, the response time for the bending of the distal extremity of the guide wire 16 is very short, i.e., in the vicinity of 1 to 2 seconds so that movement of the tip 48 of the guide wire 16 in response to movement of the handle 109 is substantially in real time. This makes it possible for the physician to establish the desired bend in the distal extremity of the guide wire 16 while it is "on the fly". Thus it is possible for a physician by operating the slide control handle 109 of the linear potentiometer 108 to cause the distal extremity of the guide wire 16 to advance through a tortuous vessel by repeated heating and cooling of the actuator wire 64 under the control of the handle 109. When the handle 109 has been returned to a home position the distal extremity of the guide wire 16 is straight and can be advanced through a stenosis. Thereafter a conventional balloon catheter is advanced over the guide wire 16 to position the balloon in the stenosis to perform an angioplasty in a conventional manner.

Since the distal extremity 68 of the actuator wire 64 lies in a plane, the bending which has been hereinbefore described will also occur in the plane of the distal extremity 68. Bending in this plane can extend from 0° to 90° and even to 180° and greater if desired by providing such a preformed memory in the actuator.

With a guide wire 16 of the present invention it is possible to provide a guide wire which has a very floppy atraumatic tip that corresponds in characteristics very similar to the floppiness of a conventional high torque floppy guide wire. However, when the actuator wire 64 is energized it will become slightly stiffer so that its stiffness is between that of a conventional high torque floppy guide wire and a conventional intermediate guide wire.

By providing such a guide wire 16 having a bendable distal extremity which can be controlled from a remote location as for example at the control console 18, it is possible to negotiate a vessel with a single pass of the guide wire 16. It is unnecessary to pull out the guide wire and reconfigure the tip as has been done in the past with respect to the high torque floppy guide wires. This greatly reduces the time required to advance the distal extremity of a guide wire into the desired location reducing the amount of time required by the physician and also decreasing the amount of X-ray exposure to the patient during fluoroscopy. Thus the time required for the entire medical procedure is reduced. The bending of the distal extremity can be accomplished by use of very small amounts of energy as for example 1 to 200 milliamperes for very small amounts of time i.e. 1–2 seconds thereby minimizing the amount of heat which is supplied to the distal extremity of the guide wire and into the blood in the vessel being negotiated. Only enough current is supplied to heat the distal extremity 68 so that very little heat is imparted to the other portions of the distal extremity of the guide wires 16. The response time is less than 2 seconds in achieving a bend ranging from any degree beyond 0° through 180° and even greater if desired. By reducing the amount of heating desired, the amount of heat that is supplied to the blood in the bloodstream passing through the vessel is minimized. This localized heating of the actuator wire 64 makes this possible.

Figure 11:
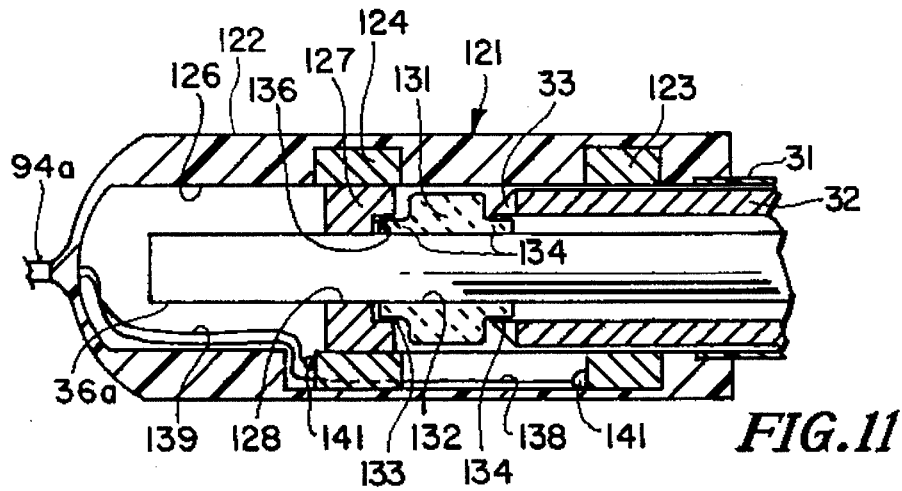
FIG. 11 is a partial side elevational view partially in section of another embodiment of a guide wire incorporating the present invention utilizing an alternative connector.

In FIG. 11, there is shown a connector 122 which can be utilized in connection with a guide wire of the type which does not have a crimped or coined end 36 as shown in FIG. 2 but which has a straight end identified as 36a in FIG. 11. As can be seen in FIG. 11, the end 36a is cylindrical or straight. The connector 122 consists of a housing 133 formed of a suitable material such as plastic. First and second spaced apart slip rings 123 and 124 formed of a suitable material such as beryllium copper are carried by the housing 133. The slip rings 123 and 124 extend into a cylindrical bore 126 provided in the housing 133. The slip ring 123 is adapted to frictionally engage the sleeve 32 provided on the proximal extremity 23 of the flexible elongate member 22. The slip ring 124 is adapted to frictionally engage a contact ring 127 also formed of a suitable material such as beryllium copper. The contact ring 127 is provided with a bore 128 which is sized so that the contact ring 127 frictionally engages the core wire 36a and is retained thereon. A cylindrical spacer 131 formed of a suitable insulating material such as plastic or a ceramic is similarly provided with a bore 132 that is sized so that the spacer 131 fractionally engages the core wire 36a. If desired the spacer 131 can be retained on the core wire 36a by suitable means such as an adhesive.

As shown in FIG. 11 to provide additional friction engagement with the core wire tip 36a, the spacer 131 can be provided with annular lips 134 extending axially therefrom with the annular lip 134 underlying the fillet 33 and with the annular lip 134 being seated within annular recess 136 provided in the contact ring 127. Insulated conductors 138 and 139 are secured to the rings 123 and 124 by solder 141 and are connected into the cable 94a which is connected to the control console 18.

If an exchange wire is utilized with a core wire of the type of core wire 36a, the extension wire can be provided with the similar construction as the connector 122. Alternatively, the contact ring 127 and the spacer 131 can be removed from the proximal extremity of the core wire 36a.

In a modified embodiment of the guide wire 16 shown in FIG. 2, the actuator wire 64 can have a greater diameter as for example a diameter of 0.003" versus the 0.0025" hereinbefore described in conjunction with the guide wire 16. This larger diameter actuator wire 64 provides a greater force to overcome the predetermined set which may be placed in the distal extremity or flat 57 of the core wire 28. As explained previously, the core wire 64 can be formed of a suitable material such as nickel titanium alloy or stainless steel which can be provided with a predetermined shape set or can be bent by the physician in the desired manner prior to insertion of the guide wire into the vessel of the patient. This makes it possible for the physician to preshape the coil spring 61 provided on the distal extremity of the guide wire. Alternatively, the coil spring 61 can be preset to a particular shape as for example a bend of 45° or 90°. With such an embodiment of the guide wire 16, it is possible for the physician to use a preset curve which he wishes to use and then to advance the distal extremity of the guide wire into the vicinity of the stenosis. Thereafter, the control handle 109 can be operated to supply energy to the actuator wire 64 to cause it to stiffen and assume a straight shape in accordance with the shape memory incorporated therein. The stiff or straight tip of the guide wire 16 can then be advanced through the stenosis.

By increasing the stiffness of the tip by increasing the current flow, the column strength of the distal extremity of the guide wire 16 is increased to make it possible to traverse the stenosis even though the stenosis may occlude or almost completely occlude the vessel. Also it may be possible with such a guide wire to cross total chronic occlusions in a vessel. Utilizing such a modified guide wire 16 makes it possible for doctors who are very familiar with shaping distal extremities of guide wires to utilize their skills in a similar manner.

In connection with the guide wire 16 of the present invention it should be appreciated that after a physician has been able to perform an angioplasty on a stenosis in a vessel of a patient, it is possible for the physician to partially retract the guide wire 16 and to thereafter advance the distal extremity of the guide wire into another vessel utilizing the same procedure. This makes it unnecessary for the physician to withdraw the guide wire in treating stenoses in multiple vessels during an angioplasty procedure. This again will reduce the time required for physician and the amount of time which the patient is subjected to fluoroscopy.

In connection with the present invention it should be appreciated that in addition to utilizing Nitinol for the actuator wire 64 in the guide wire 16 and with the core wire 28 being formed of stainless steel, the core wire can also be made out of a superelastic Nitinol or other alloys which can provide additional stiffness to the tip. A platinum foil can also be used which can be provided with a predetermined curvature which will straighten out when a current is passed through the same. The use of superelastic materials in the present application is particularly desirable because the superelastic material has a memory to return to the same shape every time the shape memory material is heated. It is very predictable in achieving the same desired angle upon heating. Thus even if the superelastic material is shaped with a predetermined memory as for example an angle 45° or 90°, it will return to such an angle when heat is applied to the same.

Polyimide coatings have been selected in connection with the present invention because they have a very high elastic strain compared to other conventional polymers. This is particularly desirable because of space limitations. It is desirable to reduce the thickness of the insulating coating to the smallest possible dimension while achieving the desired insulation. In addition, polyimides have a very good anti-friction properties. The polyimide is also a very tough material. Since it is a cross-linked polymer, it has improved adhesion characteristics to the stainless steel core wire.

In FIG. 12 there is shown a guide wire 151 incorporating another embodiment of the present invention. It differs from the guide wire 16 herein before described principally in that the inner sleeve 42 and the coil-spring 61 have been replaced by counter-wound coil assembly 152. Counter-wound coil assemblies are disclosed in co-pending application Ser. No. 08/148,005 filed on Nov. 5, 1993.

The counter wound coil assembly 152 consists of first and second counter wound coils 153 and 154 with the coil 153 being the exterior coil and coil 154 being the interior coil. The counter wound coil assembly 152 can have the suitable length as for example 30 centimeters and is secured to the distal extremity 24 of the flexible elongate tubular member 22. The two coils 153 and 154 are formed of a suitable material such as stainless steel identified as SS 304V which is characterized in that it has a very high tensile strength, it is very springy and has a very high modulus of elasticity. For the coils, a drawn ribbon is used. The ribbon has a thickness of approximately 0.00075" and a width of 0.006" to provide at least a ratio of 1 by 8 for thickness with respect to width to obtain a stiffer coil having the desired column stiffness. As can be seen from FIG. 12 of the drawings the coils 153 and 154 are wound in opposite directions with the coil 153 being wound in a clockwise direction and the coil 154 being wound in a counter-clockwise or opposite direction. This typically is accomplished by winding the outer coil 153 on a mandrel rotating in one direction as for example clockwise, releasing the ends of the wound coil 15 and putting it aside. Thereafter utilizing the same mandrel the other coil 154 is wound in the opposite or counter-clockwise direction. While the inner coil 154 is still wound on the mandrel, it can be inserted through the outer coil 153 and then released so that the outer surface of the coil 154 engages the inner-surface of the coil 153. To establish frictional engagement between the two coils 153 and 154.

The counter wound coil assembly 152 can then be mounted on the distal extremity of the inner mandrel or core wire 28 and secured thereto by suitable means such as adhesive or a solder (not shown). The other components of the guide wire 16 as hereinbefore described extend through the bore 156 in the coil assembly and the distal extremity of the flat 57 and the distal extremity 68 of the actuator wire 64 are bonded into a ball-like tip 158 in a suitable matter such as by a TEG weld. A layer 161 of a suitable material such as the polyimide can be placed over the coil assembly 152 to prevent the entrance of blood or other liquids disposed in the vessel and to which the guide wire 151 is to be inserted.

The guide wire 151 utilizing the counter wound coil assembly 152 has excellent torque transmission which is provided by the counter wound coils 153 and 154 making it possible to transfer torque in a clockwise or counter-clockwise direction as the guide wire 151 is rotated. The guide wire 151 can be utilized in the same manner as the guide wire 16 hereinbefore described. The guide wire 151 provides improved torque capabilities principally because of the counter wound coil assembly 152 on the distal extremity of the guide wire 151.

If there is sufficient room available, it should be appreciated that additional coils can be provided within the counter wound coil assembly 152. For example a third coil could be provided (not shown) within the inner-coil 154 going in the same direction as the coil 153. Similarly, a fourth coil can be provided within the additional coil and wound in the same direction as the coil 154. The use of additional counter wound coils is particularly appropriate in the larger size guide wires going from 0.018" and larger.

Another embodiment of a guide wire incorporated in the present invention as shown in FIGS. 13 and 14. The guide wire 171 is very similar to the guide wires herein-before described with the principal exception that the flexible elongate tubular member 22 in the form of a hypotube has been omitted to permit use of a larger diameter core wire that is provided to aide in torque transmission. Thus as shown in FIGS. 13 and 14, a core wire 172 has been provided of a suitable material such as stainless steel which has a suitable outside diameter such as 0.013" extending to the first taper 173 of a suitable length as for example 145 centimeters. As shown in FIG. 14, this core wire 172 is solid. The distal extremity core wire 172 is provided with various tapers of the type described in connection with the embodiment of the guide wire shown in FIG. 1 and is connected into the TEG weld 63 in the manner hereinbefore described. An insulating layer 176 is provided on the outer surface of the core wire 172 and extends from the proximal extremity to leave a cylindrical portion 177 uncovered as for example a length of one centimeter and extends towards the distal extremity and underlies a metal layer 178 provided on the core wire. The insulating layer 176 is formed with suitable materials such as a polyimide of a suitable thickness as for example 0.0003". This uncovered cylindrical portion 177 is provided for making electrical contact to the guide wire 171 to supply electrical energy to the actuator wire 64 in the matter hereinbefore described.

A conductive metal layer 178 is placed over the insulating layer 176 and extends from regions near opposite ends of the insulating layer 176. The conductive metal layer 178 can be formed of a suitable conductive material as for example 0.0005" of copper. A more suitable conductive layer can be comprised of one to two microns of nickel to serve as an adhesion layer followed by five to six microns of copper and covered by a thin layer of gold as for example layer having a thickness of less than one mil. The conductive metal layer 178 is covered with a layer 179 of a suitable insulating material such as Parylene, polyethylene or PET which leaves a cylindrical distal extremity of the conductive metal layer 178 exposed (see FIG. 13) and which has the other extremity underlying the outer sleeve 46 and bonded thereto by the adhesive 47 as described in the previous embodiments. The proximal extremity of the actuator wire 64 is bonded to the conductive metal layer 178.

Thus it can be seen in the embodiment of the guide wire 171 as shown in FIGS. 13 and 14, that electrical energy can be supplied to the actuator wire 64 by utilizing the stainless steel core wire 172 for one of the conductors by making contact with region 177 through the core wire 172 through the TEG weld 63 and then through the actuator wire 64 which is bonded to the conductive metal layer 178 to provide the other electrical connection at the distal extremity at which can make a connection to a suitable connector (not shown) so that electrical energy from the control console 18 can be supplied to the guide wire for operation in the same manner as hereinbefore described in connection with the previous embodiments.

From the foregoing can be seen that providing a conductively cladded core wire makes it possible to utilize a larger core wire or mandrel to enhance the torque characteristics of the guide wire. This particularly advantageous for small size guide wires as for example 0.014" of the type shown in FIGS. 13 and 14 as well as for smaller diameter guide wires. The construction shown in FIG. 13 and 14 is also advantageous in that it is more economical to construct.

A guide wire 201 incorporating another embodiment of the invention is shown in FIGS. 15, 16 and 17. As shown therein, the guide wire 201 consists of a flexible elongate member 202 in the form of a core wire or mandrel formed of a suitable material such as stainless steel and having a diameter ranging from 0.005" to 0.010" and preferably approximately 0.0075" and having a proximal extremity (not shown) and a distal extremity 204. The distal extremity 204 is provided with tapered and flattened portions as hereinbefore described in connection with the embodiment shown in FIG. 2. The core wire or mandrel 202 can have a suitable length as for example 180 cm.

As hereinafter described, the core wire or mandrel 202 can serve as a conductor and additional conductive means is carried by the core wire or mandrel for providing a second conductor and consists of insulation layer 206 formed of a suitable material such as a polyimide which is coated onto the outer surface of the core wire or mandrel 202. The conductive metal layer 207 is formed on the insulation layer 206 and is formed of a suitable conductive material such as silver. The silver layer 207 can be applied in a suitable manner such as by soldering or alternatively by a less expensive process called mirroring or a silver ink dip process. In this process, the insulation layer 206 is treated so as to form a proper bond with the silver to be formed thereon. This bond is formed by a coat of sugar, typically sucrose, glucose, formaldehyde, etc. This coating can be accomplished by dipping the flexible elongate member in the form of a core wire or mandrel into a room temperature bath. If for example the bath is a long chain sugar such as formaldehyde, the bath in liquid form will coat the polyimide insulating layer with a liquid layer which is then partially cured in a suitable manner such as by the use of ultraviolet light so that aldehyde groups are hanging off of the surface.

After the coating has been partially cured, the core wire or mandrel 202 can be dipped into a silver nitrate solution. Silver from the silver nitrate solution is deposited onto the coating. The formaldehyde serves to form a strong mechanical bond between the polyimide insulating layer and the silver layer to create good adhesion between the same. During the dipping process, the silver nitrate can be agitated and maintained at a desired temperature as for example 30° C. to 40° C. to cause the deposition of silver occur at a faster rate than at lower temperatures. When the silver is deposited in this manner, it will adhere more tightly to the polyimide insulation layer 206 than to the core wire or mandrel 202. The insulation layer 206 can have a suitable thickness as for example 0.5 to 2 mils and similarly the conductive metal layer 207 formed of silver can have the suitable thickness as for example 0.5 to 2 mils.

A flexible elongate tubular member 211 of the type hereinbefore described and in the form of a stainless steel hypotube is coaxially mounted on the core wire or mandrel 202. An adhesive 212 disposed on the proximal and distal extremities of the hypotube 211 to bond the hypotube to the core wire 202 to aid transmission of torsional forces between the proximal extremity of the guide wire 201 and the distal extremity.

The distal extremity of the hypotube 211 is provided with a taper 213 extending forwardly and inwardly as shown in FIG. 15. An insulation layer 216 is provided on the outer surface of the hypotube 211 and is formed of a suitable material such as a polyimide. The hypotube 211 has a suitable wall thickness, as for example 2 mils, so that for a hypotube to have an inside diameter of 0.010", the outside diameter would be 0.014".

A flexible coil assembly 221 is mounted on the distal extremity of the mandrel or core wire 202 and is secured to the distal extremity of the hypotube 211. The flexible coil assembly 221 can have a suitable length as for example 35 cm with the guide wire 201 having a total length of 180 cm. The coil assembly 221 is provided in two sections, a proximal section 222 and a distal section 223 in which the distal section can have a suitable length as for example 5 cm. The proximal section 222 of the coil assembly 221 can be formed of a less expensive material such as copper whereas the distal extremity 223 is formed of a suitable radiopaque material such as platinum or platinum tungsten alloy. The coils 222 and 223 can be formed of a wire of a suitable diameter as for example 0.0225" or 2.5 mils. Before winding of the coils, portions of the wire can be flattened to provide flattened coil sections 222a and 223a respectively, with the flattened portions being provided on the proximal extremities of the respective sections 222 and 223. As shown in FIG. 15, the flattened portions 222a are inserted into an annular space 224 provided between the interior of the hypotube 211 and the exterior of the core wire 202 and are electrically connected to the hypotube 211 by pseudo means such as solder 226. The section 222 extends coaxially over the core wire 202 and the distal section 222 abuts the proximal extremity of the section 223 which is also coaxially disposed on the core wire 202. The distal extremity of the distal section 223 is secured in a suitable manner such as a TEG weld 228 formed of a conductive material which is bonded to the distal extremity of the core wire 202 which has the insulation layer 206 removed therefrom so that it makes electrical contact with the TEG weld 228. The TEG weld 228 provides a hemispherical or rounded outer surface 229.

TEG weld 228 also makes electrical contact with an actuator member 231. The actuator member 231 in connection with the present embodiment is provided of a reduced length as for example 5 to 7 cm in comparison to approximately 20 cm for the embodiments hereinbefore described by improving radial symmetry. This aids in reducing any tendency for the guide wire to whip during use as hereinafter described. The actuator member 231 is formed of a wire 232 of a suitable Nitinol material which is covered with a layer of insulation 233 formed of a suitable material such as a polyimide. The wire 232 can have a suitable diameter, as for example 2.5 mils. The distal and proximal extremities of the actuator member 231 are not insulated and are respectively electrically coupled to the weld 228 and to the distal extremity of the coil section 222 by solder 236. It can be seen that by providing the flattened portion 223a for the distal spring section 223 it is possible to provide the necessary space for the actuator member 231.

The distal extremity of the distal coil section 223 is filled with a suitable silicone encapsulant 238 disposed between the weld 228 and an adhesive connection 239 which is provided for securing the coil section 223 to the core wire 202.

Operation and use of the guide wire 201 as shown in FIGS. 15, 16 and 17 is very similar to that hereinbefore described. However the embodiment of the guide wire 201 has certain additional advantages. As in the previous embodiment, it has a unique body design in which the core wire 202 is bonded to the hypotube 211 so as to act as a unitary structure in the transformation of torsional forces from the proximal extremity of the guide wire 201 to the distal extremity and to the flexible coil assembly 221. The tendency of the guide wire to whip is greatly minimized by the use of the conductive means for the actuator member 231 coaxially disposed in the guide wire. One of the conductors is coaxially carried by the core wire 202 and the other conductor is provided by the hypotube 211 which is also coaxially disposed in the guide wire. This overcomes any eccentricity which is provided when two separate conductors as for example conductor wires are disposed within the guide wire. The only remaining eccentricity of the guide wire as shown in FIGS. 15, 16, and 17 is that provided by the actuator member 231 which as hereinbefore described has been shortened substantially so that its offsetting effect during torsional movement of the guide wire is greatly minimized.

In the event it is desired to provide additional conductors in the guide wire, another embodiment of a guide wire 241 is shown in FIG. 18. In such an embodiment, the exterior surface of the core wire 242 could be coated with a silver layer 243 in the manner hereinbefore described followed by an insulating layer 244 followed by another silver layer 246. The silver layer 246 is covered by an insulation layer 247. All of these layers are disposed within a hypotube 248 covered by an insulation layer 249. In this manner it can be seen that a plurality of coaxial conductors can be provided on the core wire in a manner hereinbefore described and still provide the desired radial symmetry. This minimizes any tendency on the guide wire to whip during torsional rotation of the same. These additional conductors can be utilized for additional features in the guide wire for example for providing steering capabilities in the distal extremity by the use of shape memory elements in the distal extremity in a manner well known to one of ordinary skill in the art. This also serves to inhibit any preferential bending of the guide wire in one direction or another.

In connection with the foregoing invention in the event that pinholes occur in the various coaxial layers formed on the core wire and through which minuscule connections are made between the conductive layers through such pinholes, the connections can be eliminated by applying electrical energy between two layers at a time so as to fuse or evaporate any short circuits which may be present between the two conducting layers because of such connections. Vaporizing or blasting out these small connections establishes the continuity of each of the conductive layers so that it can be utilized for a conductor in the manner hereinbefore described.

Although the present conductive layers have been described principally with the use of silver, it should be appreciated that other materials can be utilized for the conductive layer. Also, a composite conductive layer can be provided as for example a layer of copper which has been coated with gold with a nickel adhesion layer there between which promotes adhesion and which also prevents migration of the copper into the gold.

In view of the foregoing it can be seen that there has been provided a guide wire which has many desirable features. The guide wire has a deflectable tip which can be deflected or bent from a remote location. The deflectable tip can have a shape memory incorporated therein which can be brought into play by the application of heat to the distal extremity. Different bends can be provided in the distal extremity. Also increased stiffness can be achieved. This makes the guide wire of the present invention very advantageous for use in traveling through tortuous vessels and for passing through totally occluded or substantially occluded vessels. This can be accomplished without withdrawing the guide wire from the vessel. Similarly a stenosis in different vessels can be addressed without completely withdrawing the guide wire or reshaping the distal extremity of the guide wire after it has been withdrawn. The guide wire also has very desirable characteristics such as being very floppy with a soft atraumatic tip. Also when desired the distal extremity can be activated to achieve additional stiffness in the distal extremity to facilitate crossing a stenosis.

What is claimed is:

1. A guide wire for use in a medical procedure in negotiating a tortuous vessel in a patient and for use with a power supply having a manual control comprising a flexible elongate tubular member having proximal and distal extremities and having a bore extending from the proximal extremity to the distal extremity, a core wire extending through the bore of the flexible elongate tubular member, a coil assembly mounted on the distal extremity of the flexible elongate member and having a distal extremity, a rounded tip carried by the distal extremity of the coil assembly, an actuator member having at least a portion thereof disposed in the coil assembly and having proximal and distal extremities, means securing the proximal extremity of the actuator member to the distal extremity of the flexible elongate tubular member, means securing the distal extremity of the actuator member to the rounded tip, said actuator member having at least a portion thereof formed of a shape memory material and incorporating a shape memory therein and capable of assuming austenitic and martensitic states, heating means disposed in the vicinity of said portion of the actuator member for heating said portion to cause it to assume the predetermined shape memory and electrical conductive means connected to said heating means and extending to the proximal extremity of the flexible elongate tubular member and being adapted to be connected to said power supply to supply energy to the heating means, said electrical means including at least one conductor exterior of the core wire and extending to the proximal extremity of the flexible elongate tubular member, said guide wire having a bendable distal extremity capable of assuming a first floppy condition when the shape memory material is in the austenitic state and a second stiffer condition and assuming the shape memory when the shape memory material is in the martensitic phase so that by operation of the manual control the distal extremity of the guide wire can be caused to repeatedly assume said first and second conditions to and in negotiating the distal extremity of the guide wire through the tortuous vessel.

2. A guide wire as in claim 1 wherein said predetermined shape memory is a straight shape.

3. A guide wire as in claim 1 wherein said predetermined shape memory is a curved shape.

4. A guide wire as in claim 1 together with means for securing the distal extremity of the core wire to the rounded tip.

5. A guide wire as in claim 4 wherein said core wire has a predetermined bend therein and wherein said actuator member is capable of creating a force sufficient to overcome the bend in the core wire.

6. A guide wire as in claim 1 wherein said portion has a flattened distal extremity so that bending can only occur in a plane substantially perpendicular to the flattened distal extremity.

7. A guide wire as in claim 6 wherein said actuator member is formed of a shape memory material together with a layer of electrically conductive material overlying the shape memory material to permit at least a portion of the electrical energy to bypass at least a portion of the shape memory material.

8. A guide wire as in claim 1 wherein said electrically conductive means includes said flexible elongate element and said core wire together with insulating means insulating said core wire from said flexible elongate member.

9. A guide wire as in claim 6 wherein said core wire is provided with a flattened distal extremity which lies parallel to the flattened distal extremity of the actuator member.

10. A guide wire as in claim 1 wherein said coil assembly includes a protective covering to prevent liquids from entering into the coil assembly.

11. A guide wire as in claim 1 wherein said coil assembly includes counter wound coils.

12. A guide wire as in claim 1 wherein the mass of said portion to be heated is relatively small so that the tip can move in substantially real time.

13. A method for using a single guide wire for passing through a stenosis in a vessel in a human body, the guide wire having a deflectable tip, a core wire connected to the deflectable tip and having an actuator member secured to the deflectable tip and having a portion thereof formed of a shape memory material and being adapted to have incorporated therein a predetermined memory and means for supplying to the heat to said portion of the actuator element, the method comprising forming a predetermined shape in the shape memory element, introducing the deflectable tip of the guide wire while it is soft and flexible into the vessel and advancing the tip of the guide wire in the vessel until a bend is reached in the vessel, supplying heat to the shape memory element to cause a bend to occur in the deflectable tip, continuing advancement of the tip with the bend therein through the bend in the vessel until the tip is in the vicinity of the stenosis, causing the deflectable tip to assume a relatively straight and stiffer condition and advancing the tip through the stenosis while the tip is in the stiffer condition.

14. A method as in claim 13 together with the step of forming the deflectable tip with a predetermined straight shape.

15. A method as in claim 13 together with the step of forming the deflectable tip with a predetermined curved shape.

16. A method as in claim 13 together with the step of forming a predetermined shape into the deflectable tip and applying heat to the actuator element to cause it to overcome the force of the predetermined shape formed in the deflectable tip.

17. A guide wire for use in a medical procedure in negotiating a tortuous vessel in a patient and for use with a power supply having a manual control comprising a flexible elongate solid core wire having proximal and distal extremities, a coil assembly mounted on the distal extremity of the core wire having proximal and distal extremities, a tip carried by the distal extremity of the coil assembly, an actuator member having at least a portion thereof disposed in the coil assembly and having proximal and distal extremities, means securing the distal extremity of the actuator member to the tip, said actuator member having at least a portion thereof formed of a shape memory material and capable of assuming austenitic and martensitic states, electrical means adapted to receive electrical energy from the power supply under the control of the manual control for supplying heat to said portion of the actuator member to cause it to shift from an austenitic state to a martensitic state, said electrical means including at least one conductor carried by the core wire exterior of the core wire to the proximal extremity of the core wire, said at least one conductor serving as one conductor and said core wire serving as another conductor for supplying the electrical energy for causing heating of said portion of the actuator member.

18. A guide wire as in claim 17 together with means for securing the proximal extremity of the actuator member to the core wire.

19. A guide wire as in claim 18 wherein said electrical means includes a layer of insulating material formed on the exterior surface of the core wire extending from the proximal extremity to near the distal extremity, a metal conducting layer overlying the insulating layer extending from the proximal extremity of the core wire to near the distal extremity of the core wire and a coating overlying the conductive layer.

20. A guide wire as in claim 17 wherein the distal extremity of said core wire is provided with at least one taper and wherein said coil assembly includes a coil having proximal and distal extremities, said tip being secured to the distal extremity of the coil, an insulating tube secured to the proximal extremity of the coil and overlying at least a portion of the insulating layer on the core wire and being in general alignment with said at least one taper provided in the core wire so that the outer surface of the insulating tube and the coating have outer diameters which are substantially the same so as to provide a guide wire having a substantially continuous flush outer surface.

\* \* \* \* \*

UNITED STATES PATENT AND TRADEMARK OFFICE
CERTIFICATE OF CORRECTION

PATENT NO. : 5,542,434
DATED : August 6, 1996
INVENTOR(S) : Imran et al.

It is certified that error appears in the above-identified patent and that said Letters Patent is hereby corrected as shown below:

Column 7,
Lines 1-2, cancel "austenitic state to a martensitic state" and substitute therefor -- martensitic state to an austenitic state --

Column 8,
Line 21, cancel "fractionally" and substitute therefor -- frictionally --
Line 24, cancel "friction" and substitute therefor -- frictional --

Column 10,
Line 9, cancel "153. To" and substitute therefor -- 153 to --.
Line 19, cancel "matter" and substitute therefor -- manner --.
Line 55, after "extremity" insert -- of the --.

Column 11,
Line 19, cancel "matter" and substitute therefor -- manner --.

Column 12,
Line 16, after "silver" insert -- to --.
Line 61, cancel "pseudo" and substitute therefor -- suitable --.

Column 15,
Lines 8-9, cancel "austenitic" and substitute therefor -- martensitic --
Line 11, cancel "martensitic" and substitute therefor -- austenitic --

Column 16,
Line 34, cancel "an austenitic state to a martensitic state" and substitute therefor -- a martensitic state to an austenitic state --

Signed and Sealed this

Second Day of November, 2004

JON W. DUDAS
*Director of the United States Patent and Trademark Office*